United States Patent [19]

Herlitze et al.

[11] Patent Number: 4,968,308
[45] Date of Patent: Nov. 6, 1990

[54] COUPLING ASSEMBLY

[75] Inventors: Gerhard Herlitze, Baunatal; Klaus-Joachim Schmidt, Ahnatal; Egon Lesemann, Melsungen; Hans-Otto Maier, Melsungen; Karl-Friedrich Voges, Melsungen; Heinz Wiegel, Alheim-Heinebach, all of Fed. Rep. of Germany

[73] Assignee: B. Braun Melsungen AG, Melsungen, Fed. Rep. of Germany

[21] Appl. No.: 345,996

[22] Filed: May 2, 1989

[30] Foreign Application Priority Data

Jun. 14, 1988 [DE] Fed. Rep. of Germany ... 8807699[U]

[51] Int. Cl.$^5$ ............................................. A61M 25/00
[52] U.S. Cl. ...................................... 604/280; 604/243
[58] Field of Search ............... 604/280, 242, 243, 158, 604/283, 240, 241, 164, 165

[56] References Cited

U.S. PATENT DOCUMENTS 3,903,885 9/1975 Fuchs ..................................... 604/158
4,187,848 2/1980 Taylor ................................... 604/243

Primary Examiner—John D. Yasko
Attorney, Agent, or Firm—Spensley Horn Hubas & Lubitz

[57] ABSTRACT

A coupling assembly for connecting a flexible catheter to the hub cone of a sheath for inserting the catheter into a punctured body cavity consists of a housing having two separable housing halves which jointly form a passage for the catheter and have their patient-proximal front end provided with a tip for insertion into the hub cone of the sheath. In the passage, there is arranged shaped sealing formed as a hollow cylinder of an elastic material, provided as a tube tightly surrounding the catheter and having a thickened head portion. The outer diameter of the head portion is adapted to the outer diameter of the tip of the housing, and the tube is inserted into a widened portion of the passage such that the head portion of the tube abuts against the front face of the tip. Such a shaped sealing acts as a closing stopper which prevents that blood can travel rearward between the separating slits of the housing halves and escape to the outside.

6 Claims, 2 Drawing Sheets

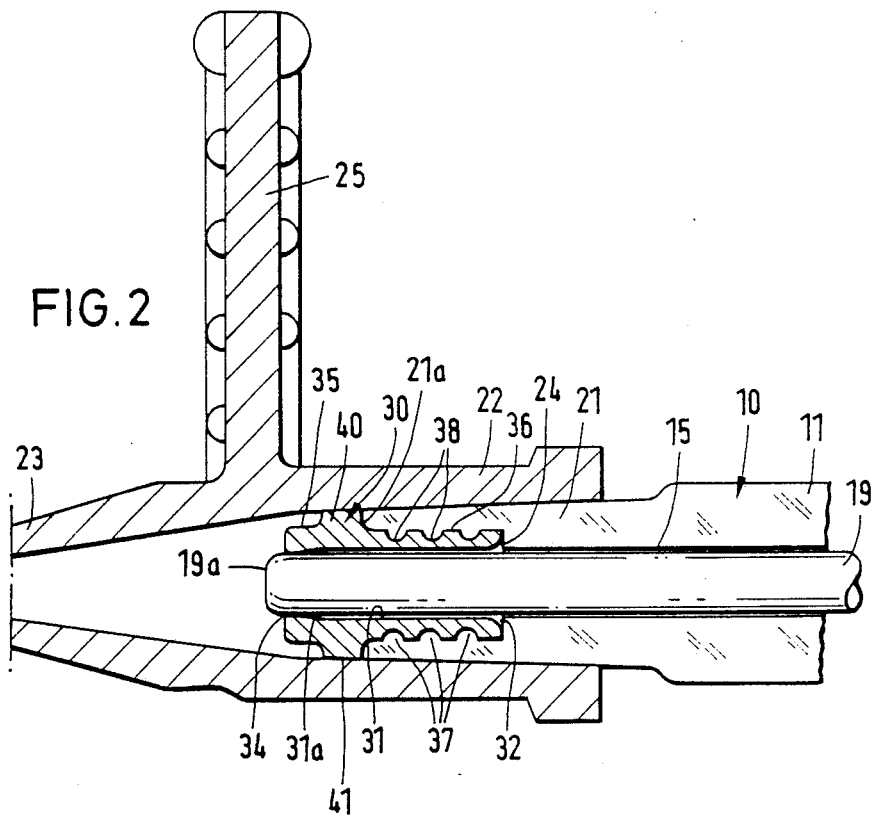
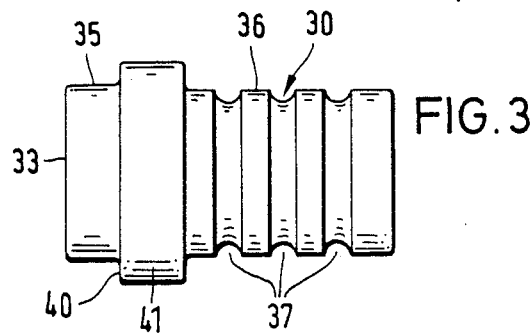
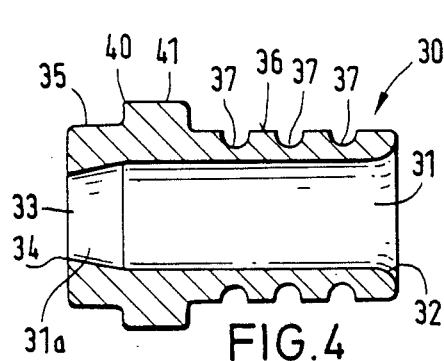
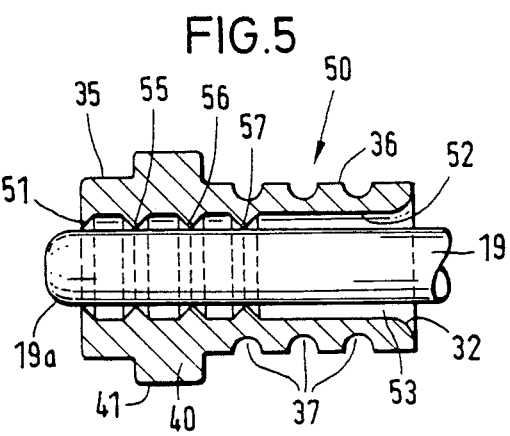

COUPLING ASSEMBLY

BACKGROUND OF THE INVENTION:

1. Field of the Invention:

The invention is directed to a coupling assembly.

2. Description of Related Art:

A known coupling assembly is described in U.S. Pat. No. 3,903,885. In this known coupling assembly, the shaped sealing, made of an elastic rubber material, is cap-shaped and has a conical bottom. The conical bottom is arranged at the rear end of the passage of the coupling assembly, averted from the tip of the housing. The inner diameter of the shaped sealing is considerably larger than the outer diameter of the catheter, which is sealingly guided through a central bore in the conical bottom. The conical bottom is flexible, so that it is drawn rearward and thus is tilted over when the catheter is withdrawn, thereby exerting a stopping effect on the catheter by radially narrowing the bore.

For removing the coupling assembly after successfully positioning the catheter, both halves of the coupling assembly housing can be radially separated after the catheter tip has been drawn out of the hub cone of the sheath. The shaped sealing is slit longitudinally so that after taking apart both halves of the housing of the coupling assembly, the catheter can also be radially removed from the shaped sealing, which is firmly attached to one half of the housing.

By the coupling assembly, a catheter is connected to the hub cone of a sheath (for example, a "Braunüle"), which sheath after puncturing, e.g., of a blood vessel, has been inserted thereinto. The end of the coupling assembly averted from the sheath can have a protecting cover applied thereto for protecting the catheter against contamination. The catheter is introduced into the blood vessel through the coupling assembly and the sheath.

According to the state of the art, the interior of the sheath and of the coupling assembly are in communication with the blood circulation of the patient between the time that the coupling assembly is coupled to the hub cone of the sheath until the time that the catheter is advanced into the tip of the sheath. Due to the excess pressure of the blood circulation, blood issues to the outside from the separating slits between both halves of the housing of the coupling assembly. This makes it possible that personnel may be contaminated by the blood of the patient while the catheter is being positioned. In this manner, there are spread contagious diseases being transmitted by blood.

In the known coupling assembly, the issuing of blood out of the separating slits between the two halves of the housing is not prevented, because the shaped sealing is slit longitudinally and because it is arranged at the rear end of the passage. Consequently, during the critical time period, a large part of the length of the passage is filled with blood which can freely exit to the outside in a radial direction. The known shaped sealing is effective too late and, for spatial and functional reasons, does not allow relocation to the front end.

It is an object of the present invention to improve the coupling assembly in such a manner that radial issuing of blood from the separating slits between both halves of the housing is reliably prevented.

SUMMARY OF THE INVENTION

In accordance with the present invention, this and other objectives are achieved by providing a shaped sealing formed as a tube tightly surrounding the catheter. The tube has a thickened head portion with an outer diameter adapted to the outer diameter of the tip of the housing. The tube is inserted into a widened portion of the passage such that the head portion of the tube abuts against the front face of the tip.

In this manner, the shaped sealing forms a closing stopper at the tip of the housing of the coupling assembly. The closing stopper prevents blood from travelling rearward between the separating slits of the halves of the housing and penetrating to the outside. With the tip of the coupling assembly plugged into the hub cone of the sheath, the outer surface of the thickened head portion sealingly abuts against the inner surface of the hub cone so that there is effected a sealing against blood backflow at this circumferential area. Within the tube of elastic rubber material, the tip of the catheter is fitted to be axially displaceable but tightly enclosed so that no gap exists between the catheter and the inner wall of the tube and the oncoming flow of blood is guided directly into the lumen of the catheter.

Thus, the catheter itself circumferentially seals the passage of the coupling assembly over the entire length of the passage. Escape of blood through the separating slits between both halves of the coupling-assembly housing is effectively eliminated by this double sealing. It is a further advantage of the present invention that during the period of non-use of the coupling assembly, when the catheter tip is inserted into the shaped sealing, (i.e., during the time period between the manufacturing of the coupling assembly and the catheter until the time of application), the elastic rubber material of the tube cannot exhaust by inner tension. This is because the inner diameter of the tube and the outer diameter of the catheter are adapted to each other in such a manner that neither the one nor the other member is subjected to radial tension. Thereby, the sealing effect of the tube of the shaped sealing is maintained for a long time with regard to both the hub cone of the sheath and the catheter.

For improving the sealing between the outer circumference of the catheter and the inner wall of the tube of the shaped sealing, one embodiment of the invention provides that a sealing lip may be formed in a radially inward direction at the front and/or the rear edge of the tube. The sealing lip preferably has a thin edge contacting the outer surface of the catheter and provides a sealing effect without hindering the easy motion of the catheter during advance thereof. The sealing lip can be formed of the narrowed opening of a taper cone of the circular cylindrical channel of the tube. This is advantageous because such a sealing lip is not excessively flexible and even under extreme conditions endures longer periods of non-use with the catheter inserted therein.

In another embodiment, it is provided that the sealing tip is arranged as an annular lamella and that a plurality of such lamellae are axially distributed over the length of the circular cylindrical channel of the tube. These lamellar sealing lips are distinguished by outstanding flexibility in the axial and radial direction, which can be favorable for special catheters and special applications. Possible weaknesses of the sealing due to larger resilience are compensated by a succession of a plurality of such sealing lips. The sealing lips can be arranged at equal or different distances to each other.

For preventing axial displacement of the tube in the tip of the housing, complementary profiles may be provided on the outer circumference of the tube and in the wall of the widened portion of the passage, which complementary profiles engage each other but are detachably connected to each other. Said complementary profiles preferably consist of annular grooves at one member and annular ribs at the other member, the annular grooves being advantageously provided at the tube. Since the outer circumference of the tube is free of projections, this is suitable when the tube of the shaped sealing is used for safely fixing the catheter after the catheter has been inserted and correctly positioned and both halves of the housing of the coupling assembly, drawn out of the hub cone of the sheath, have been separated and the sheath has been removed from the catheter. In this case, the tube and thus the catheter can be safely sutured onto the skin of the patient by suture material which is wound into the surrounding annular grooves of the tube. The tube prevents constriction and shearing, respectively, of the catheter by the seam.

BRIEF DESCRIPTION OF THE DRAWINGS

A detailed description of several preferred embodiments of the invention will be made with reference to the accompanying drawings.

FIG. 2 shows the shaped sealing of the arrangement of FIG. 1 in a larger scale.

FIG. 3 shows a plan view of the shaped sealing according to FIG. 2.

FIG. 4 shows a longitudinal section through the shaped sealing according to FIG. 3.

FIG. 5 shows a longitudinal section through a second embodiment of the shaped sealing.

DESCRIPTION OF THE PREFERRED EMBODIMENTS

Figure 1:
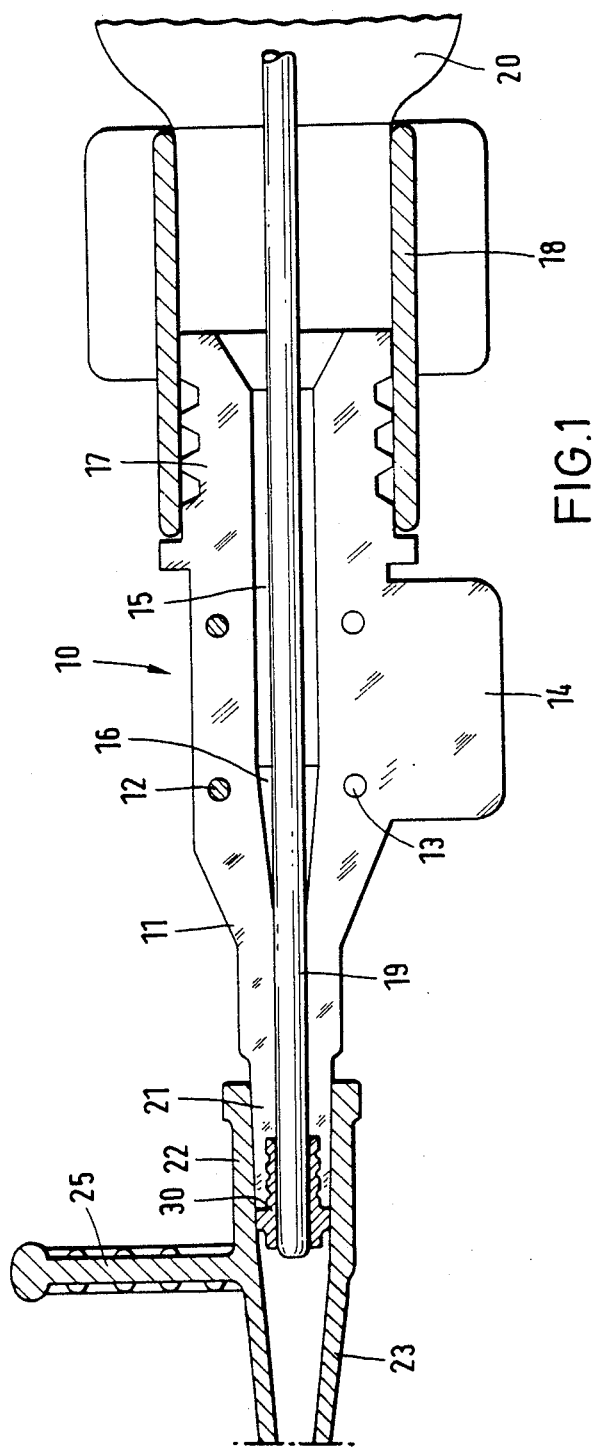
FIG. 1 shows a partial plan view of the inner side of a half of an embodiment of a coupling assembly having the hub cone of a sheath connected to its tip and having a protecting cover for a catheter connected to its end distant from the patient.

The following detailed description is of the best presently contemplated mode of carrying out the invention. This description is not to be taken in a limiting sense, but is made merely for the purpose of illustrating the general principles of the invention. The scope of the invention is best defined by the appended claims.

As illustrated in FIG. 1, a coupling assembly 10, preferably made of a comparatively hard plastic material, has its housing divided into two halves 11 adapted to be pulled apart in a radial direction. For reasons of clarity, only one of the halves 11 is shown. The opposite plane surfaces of the identical housing halves 11 are provided with pins 12 and holes 13 for mutual engagement.

Further, each half 11 of the housing has a grip plate 14 directed radially outwards. When the housing halves 11 are assembled to form a coupling of circular section, one grip plate 14 is arranged on one side and the other grip plate 14 is arranged substantially in the same plane on the other side, so that the user can seize one grip plate 14, respectively, with each hand and push the two housing halves apart radially.

In each housing member 11, there is arranged a longitudinal half of a central straight passage 15. When the coupling assembly 10 is in the closed condition, the passage 15 consists of a rearward circular cylindrical portion, a central conical portion and a forward circular cylindrical portion of a smaller diameter.

The distal or rear end of the coupling assembly 10 is provided with a cylindrical plug-on member 17 which is interrupted by circumferential grooves and onto which a clamping ring 18 is sealingly shifted. The clamping ring 18 has tightly and firmly connected thereto a longitudinally extending protecting cover 20 of thin foil containing a flexible catheter 19 to be shifted through the assembly into a blood vessel.

The other or proximal end of the coupling assembly 10 forms a tip 21 at the side of the patient, arranged as an outer cone having a circular inner diameter substantially adapted to the outer diameter of the catheter 19. The tip 21 is firmly but detachably inserted into the hub cone 22, which is provided with a laterally directed plate 25. The clamping ring 18 and the hub cone 22 cause both housing halves 11 to be tightly pressed against each other. Nevertheless, the two separating slits which remain between the housing halves 11 are not so tight that blood (flowing out by the overpressure of blood circulation) is prevented from issuing out of the coupling assembly 10 when the sheath 23 is inserted into a blood vessel.

For eliminating such escape of blood, a shaped sealing, in the form of a tube 30 preferably of elastic rubber material, is inserted into the tip 21 of the coupling assembly 10, namely into a widened portion at the front end of the passage 15. The shaped sealing or tube 30 is axially stable but can be removed after taking apart both halves 11 of the housing.

The tube 30 is a thick-walled body substantially shaped as a circular cylinder. A coaxial channel 31 of circular, cylindrical configuration leads through the tube 30. The diameter of the channel 31 substantially corresponds to the diameter of the front portion of the passage 15 of the coupling assembly 10. The front portion is adapted to the outer diameter of the catheter 19 in such a manner that the catheter 19 is freely displaceable in the axial direction. The rear end of the channel 31 is provided with a funnel-like widened portion 32 for facilitating insertion of the catheter. The front end merges into an even cone taper 31a which ends in a narrowed opening 33 that is surrounded by a sealing lip 34 arranged in a radially inward direction.

Behind a short cylindrical portion 35 having a rounded front edge, the tube 30 is provided with a thickened head portion 40 which is directed radially outwardly in the manner of an annular bead and has a plane circumferential surface 41 substantially parallel to the longitudinal axis of the tube 30. The diameter of the head portion 40 substantially corresponds to the narrowed inner diameter of the hub cone 22 of the sheath 23 and to the outer diameter of the front end of the housing tip 21. The head portion 40 is adjoined to a longer cylindrical portion 36 of the tube 30. This portion 36 is interrupted by three parallel annular grooves 37 which are separated from each other by cylindrical circumferential portions arranged therebetween. The portion 36 of the tube 30 sticks in the widened portion of the passage 15 of the tip 21 of the coupling assembly 10 in such a manner that the rear edge of the head portion 40 of the tube lies against the front face 21a of the tip 21 and the distal end of the tube 30 abuts a shoulder 24 at the inner end of the widened portion. In the inner surface of the widened portion of the passage 15, the annular grooves 37 and their positive intermediate profiles engage with complementary annular ribs 38 and the negative intermediate profiles thereof so that the tube 30 cannot be displaced in the axial direction. Irrespective of this arrangement, the tube 30 is not fastened in the tip 21 so that it can be removed when the coupling assembly 10 is separated.

The coupling assembly 10, preferably enclosed in a germ-tight packing, is made available to the user with the catheter 19 inserted therein and the protecting cover 20 connected thereto. In this configuration, the tip 19a of the catheter 19 of arbitrary length slightly projects outwardly beyond the sealing lip 34 of the tube 30. When, upon successful puncturing of a blood vessel, the sheath 23 protrudes into the blood vessel, the tip 21 of the coupling assembly 10 is lightly inserted into the hub cone 22 in order to fasten the catheter 19. Thereby, the circumferential surface 41 of the head portion 40 of the tube 30 sealingly abuts the inner surface of the hub cone 22 so that a closed sealing ring is arranged in advance of the front face 21a of the tip 21 of the two-part coupling assembly 10. The sealing ring, by pressing its circumferential surface 41 against the inner surface of the hub cone 22, prevents blood, flowing back through the sheath 23, from leaking into the separating slits between both halves 11 of the housing. The sealing lip 34 abutting the outer surface of the catheter seals the cavity in the hub cone 22 from within against the passage 15, thus safeguarding that no blood issues to the outside from the separating slits between both housing halves 11. Immediately after inserting the tip 21 into the hub cone 22, the catheter 19 is advanced within the sheath 23, and at this instant the sealing at the tip 21 of the coupling assembly 10 is relieved.

In the embodiment illustrated in FIG. 5, the outer configuration of the tube 50 corresponds to the embodiment of FIGS. 1 to 4. The difference lies in the shaping of a sealing lip at the front edge of the tube 50. This surrounding sealing lip is provided as a thin annular lamella 51 of triangular section, which is directed radially inwardly from the inner surface 52 of the cylindrical channel 53 of unchanged diameter. The diameter of the channel 53, although slightly oversized, substantially corresponds to the diameter of the passage 15 in the tip 21 of the coupling assembly 10, through which passage the catheter is advanced. At the exit of the catheter 19 from the tube 50, the lamella 51, having its small edge abutting against the outer circumference of the catheter 19, provides a sealing against an outflow of blood from the sheath. For intensifying the sealing effect against the passage 15, three further inner lamellae 55, 56 and 57 are provided in addition to the outer lamella 51. The additional lamellae extending uninterruptedly all around and each being of triangular section so as to provide a sharp sealing edge.

When the catheter 19 has been inserted and is correctly positioned, the tip 21 of the coupling assembly 10 is pulled out of the hub cone 22 of the sheath 23, and the two halves 11 of the housing are separated from each other and removed. The tube 30 or 50, respectively, of the shaped sealing remains on the catheter 19. In a next step, the sheath 23 is drawn out of the puncturing channel and shifted back to a hub (not shown) at the distal end of catheter 19. During this displacement, the hub 30 or 50, respectively, is carried along and, due to its small size, is received in hub cone 22 so that it presents no obstacle during this movement.

When using a sheath 23 being separable longitudinally, which is taken off radially from the positioned catheter 19, the tube 30 or 50, respectively, serves for fixing the catheter 19 after removing the sheath 23. To this purpose, suture material is wound into the annular grooves 37 of the tubes 30 or 50, and the tube 30 or 50 is sutured to the skin of the patient. At the same time, it is prevented that the catheter 19 is constricted or damaged by the seam.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A coupling assembly for connecting a catheter to the hub cone of a sheath, the coupling assembly comprising:
    a housing including two separable housing portions forming a passage for the catheter, the passage having a widened portion,
    a tip defined at one end of the housing adjacent the relatively wider portion of the passage, the tip having an outer diameter and a front face and being configured to be inserted into the hub cone of the sheath,
    a tube of elastic material configured to tightly surround the catheter in the passage, the tube including a head portion having an outer diameter substantially equal to the outer diameter of the tip of the housing, the head portion being configured to abut the front face of the tip when the tube is inserted in the widened portion of the passage.

2. A coupling assembly for connecting a catheter to the hub cone of a sheath, the coupling assembly comprising:
    a housing including two separable housing portions forming a passage for the catheter, the passage having a widened portion,
    a tip defined at one end of the housing adjacent the relatively wider portion of the passage, the tip having an outer diameter and a front face and being configured to be inserted into the hub cone of the sheath,
    a tube configured to tightly surround the catheter in the passage, the tube including a head portion having an outer diameter substantially equal to the outer diameter of the tip of the housing, the head portion being configured to abut the front face of the tip when the tube is inserted in the widened portion of the passage, wherein the tube further comprises an edge defining a radially inward directed sealing lip.

3. A coupling assembly according to claim 2, wherein the tube further defines a cylindrical channel terminating in a tapered cone having a narrowed opening, the sealing lip being formed at the narrowed opening of the tapered cone.

4. A coupling assembly according to claim 2, wherein the tube further defines a cylindrical channel and further comprising a plurality of annular lamellae axially distributed along the cylindrical channel, the sealing lip being formed on one of the plurality of annular lamella.

5. A coupling assembly according to claim 1, wherein the outer circumference of the tube defines a first profile and the wall of the widened portion of the passage defines a second profile, the first and second profiles being configured for mutual engagement.

6. A coupling assembly for connecting a catheter to the hub cone of a sheath, the coupling assembly comprising:
 a housing including two separable housing portions forming a passage for the catheter, the passage having a widened portion,
 a tip defined at one end of the housing adjacent the relatively wider portion of the passage, the tip having an outer diameter and a front face and being configured to be inserted into the hub cone of the sheath,
 a tube configured to tightly surround the catheter in the passage, the tube including a head portion having an outer diameter substantially equal to the outer diameter of the tip of the housing, the head portion being configured to abut the front face of the tip when the tube is inserted in the widened portion of the passage, wherein the outer circumference of the tube defines a first profile and the wall of the widened portion of the passage defines a second profile, the first and second profiles being configured for mutual engagement, wherein one of the first and second profiles comprise a plurality of annular grooves and the other of the first and second profiles comprise a plurality of annular ribs.

* * * * *